United States Patent [19]

Kamada et al.

[11] Patent Number: 4,916,081

[45] Date of Patent: Apr. 10, 1990

[54] ASSAY METHOD AND APPARATUS OF IMMUNE REACTION

[75] Inventors: Satoru Kamada, Yamato; Shuji Iwasaki, Machida, both of Japan

[73] Assignee: Toyo Soda Manufacturing Co., Ltd., Shinnanyo, Japan

[21] Appl. No.: 69,968

[22] Filed: Jul. 6, 1987

[30] Foreign Application Priority Data

Jul. 4, 1986 [JP] Japan ................. 61-157605

[51] Int. Cl.$^4$ .......................................... G01N 33/553
[52] U.S. Cl. ....................... 436/526; 422/68; 436/805; 436/806; 436/807; 436/518
[58] Field of Search ............... 436/526, 805, 806, 807, 436/518; 422/68

[56] References Cited

U.S. PATENT DOCUMENTS

| | | | |
|---|---|---|---|
| 4,092,116 | 5/1978 | Giaever | 435/7 X |
| 4,177,253 | 12/1979 | Davies et al. | |
| 4,452,773 | 6/1984 | Molday | |
| 4,454,234 | 6/1984 | Czerlinski | |
| 4,698,302 | 10/1987 | Whitehead | 435/94 |
| 4,728,500 | 3/1988 | Higo | 436/518 X |
| 4,745,077 | 5/1988 | Holian | 436/526 |

FOREIGN PATENT DOCUMENTS

| | | | |
|---|---|---|---|
| 2905434 | 8/1979 | European Pat. Off. | |
| 0030087 | 6/1981 | European Pat. Off. | 436/526 |
| 0177813 | 4/1986 | European Pat. Off. | |
| 0180384 | 5/1986 | European Pat. Off. | |
| 0211436 | 2/1987 | European Pat. Off. | |
| 0216177 | 4/1987 | European Pat. Off. | |

OTHER PUBLICATIONS

Methods in Enzymology, vol. XXXIV, "Affinity Techniques", Covalent Linkage of Functional Ligands, and Proteins to Polyacrylamide Beads, John K. Inman, pp. 30–58, 1974.

*Primary Examiner*—Christine M. Nucker
*Assistant Examiner*—Karen I. Krupen
*Attorney, Agent, or Firm*—Oblon, Spivak, McClelland, Maier & Neustadt

[57] ABSTRACT

An immunoassay method and apparatus includes the vibration of beads within a cell, the beads having a complex of a substance conjugated with an enzyme as a marker on the surface thereof, and using an optical measurement device to quantatively determine the amount of the marker in the cell. The vibration is provided by including a magnetic material in the beads and causing a magnetic field to move within the cell. The vibrations have at least a component transverse to a measurement direction of the optical measurement device. The movement of the magnetic field in the cell is caused by the reciprocation of a bar having magnets thereon and in a position adjacent to the cell.

15 Claims, 2 Drawing Sheets

ASSAY METHOD AND APPARATUS OF IMMUNE REACTION

BACKGROUND OF THE INVENTION

1. Field of the Invention

The present invention relates to an assay method for measuring immune reactions and to its apparatus, which is used to detect a very small amount of organic material.

2. Discussion of Background

As immunological means used for detecting a very small amount of organic material, a great number of studies and propositions on assay methods for detecting immune reactions have been recently made, including radioimmunoassay, fluorescent antibody method, enzyme antibody method, enzymeimmunoassay, etc.

In these representative test methods, either an antigen or an antibody (or anti-immunoglobulin), which undertakes a specific reaction, is conjugated with an appropriate marker, the complex of the antigen-antibody-marker or antibody-antigen-marker is formed, and the amount of the complex is quantitatively detected by measuring the marker as a criterion. The complex is formed by binding to the surface of a cell on which either an antigen or an antibody is fixed, or to the surface of a bead (particle) which is charged into a cell and on which either an antigen or antibody is fixed.

In other methods excepta radioimmunoassay using a radioactive substance as a marker, a fluorescent substance or a luminescent substance used as a marker is directly detected optically, or the catalytic activity of an enzyme used as a marker is revealed by the addition of an appropriate substrate and absorbance, fluorescence or luminescence is determined optically.

In various means for optical determination, the principle is that a microtiter plate serving as a cell or a sample reaction chamber, or a reactor (referred to as a cell hereinafter) composed of a separate test cup is placed opposite to the optical system, which receives reflected light from the cell, for use in determination of the intensity of light.

Since the amount of samples to be tested in immune reactions is extremelysmall, usually less than $10^{-13}$ mol/l, factors causing technical errors in the test should be excluded as much as possible even if precise equipment is employed in the aforesaid optical system.

The present inventors made various investigations from these points of view, and have learned that in the test method using a bead, which has been known as a method for detecting the immune reaction, beads existing in the cell affected technical errors in the test; that is, since the measuring area in the optical system which receives the reflected light from the cell is, in general, limit as to the measuring are within the cell, whether or not the bead exists within the measuring are of the optical system is considered to have an influence on measurement.

SUMMARY OF THE INVENTION

From those points of view, in a test method where immune reactions are performed on the surface of beads filled in a cell, the object of the present invention is to obtain an effective method, which makes technical errors in optical determination as small as possible, and to supply an apparatus fulfilling the requirements.

A feature of the present invention is to form a complex of the enzyme conjugate due to the antigen-antibody reaction on the surface of the beads filled in a cell (i.e. the complex of the enzyme labeled antibody or antigen with an antigen, antibody, or antigen-antibody), and to detect the amount of the complex by optical means while vibrating the beads within the cell. An apparatus according to this invention is composed of a cell which forms a reacting chamber where the antigen-antibody reaction takes place, the beads having a binding surface for an antigen or antibody in the cell and containing a magnetic substance, a magnet device which applies a moving magnetic field or force to the beads in the cell from outside of the cell and so causes them to vibrate, and an optical system by which the intensity of the light from inside the cell is measured. At least a component of the vibration direction is traverse to a detection direction.

The vibration of beads within the cell according to the present invention will lead to a levelling of the existence probability of beads in the limited area for optical measurement within the cell and to the elimination technical errors derived from the uneven disposition of beads in the cell. The frequency of vibration of beads, therefore, ranges usually from 10 cycles per minute to 800 cycles per minute, preferably 60 cycles per minute to 360 cycles per minute, and the amplitude of vibration is desired to be high enough to spread beads over the whole area in the cell. Any vibration, including reciprocating motion, circular motion, elliptic motion, and S-curve motion, can be permitted.

Vibration of the beads alone within the cell in the present invention was based on the fact that the mechanical vibration of the test cup itself as a cell will cause a liquid sample to scatter outside of the cell and will inadequately vibrate the beads.

The beads used in the apparatus according to the present invention contain a magnetic substance, preferably a paramagnetic substance, migrating by the magnetic action which produces vibration. Preferably, a powdered magnetic substance such as Mn-Zn-ferrite is bound to the beads with synthetic resin binders, such a polystyrene and EVA, the surface of beads possessing such functional groups as amino, hydroxy, epoxy, and aldehyde by polymerizing a glycidylmethacrylate polymer. Binding of antigens or antibodies to the surface of the beads may be carried out by a known method.

The magnetic apparatus generating the magnetic action by which the bead vibrate, can be composed of a reciprocating rod to which magnets are fixed and positioned close to the position where the test cup is placed, or an electromagnet.

The present invention can be applied to various immunoreaction methodsusing beads and measuring optically, examples being a method in which fluorescent substances (fluroesceine, etc.) or luminescent substances (isoluminole, luminole, etc.) are used as a marker and the intensity of light is measured, and another method in which enzymes such as β-D-galactosidase, alkaline phosphatase, glucoseoxidase, and peroxidase are used as a marker and the fluorescence or absorbance of a substrate on receiving the action of the enzyme activity is measured.

BRIEF DESCRIPTION OF THE DRAWINGS

Further objects and features of the present invention will become apparent from the following detailed description of the preferred embodiment thereof with reference to the accompanying drawings.

DETAILED DESCRIPTION OF THE PREFERRED EMBODIMENT

Figure 1:
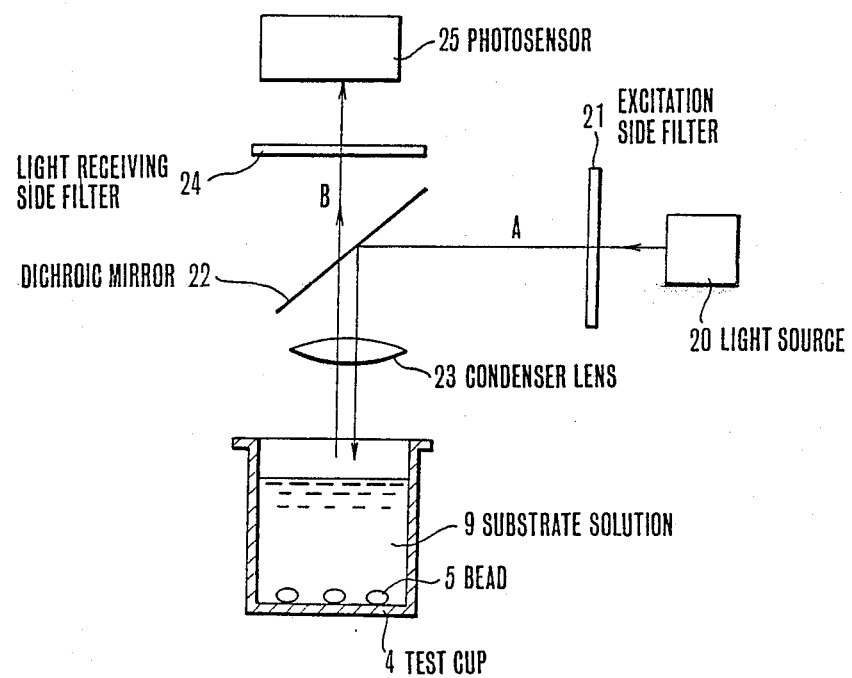
FIG. 1 shows the outline of constituents of the optical measuring apparatus explaining an embodiment of the present invention.

The following will describe an embodiment of the present invention according to the drawings.

In the drawings, 1 is a test plate which can be carried on the conveyance way 3 and has a great number of opening 2 for use in supporting a cup.

A test cup 4 is inserted and fixed to the opening 2; in the present embodiment, it is made of an opaque and magnetically permeable material obtained from a polystyrene resin containing graphite, is a cylinder cup of the upwardly opened type, and serves as a cell which is a reacting chamber.

Bead 5 are added to the cup 4, which beads contain a magnetic substance and at the surface of which a first antibody which specifically binds to the sample to be tested has been bound according to a known method.

Figure 2A:
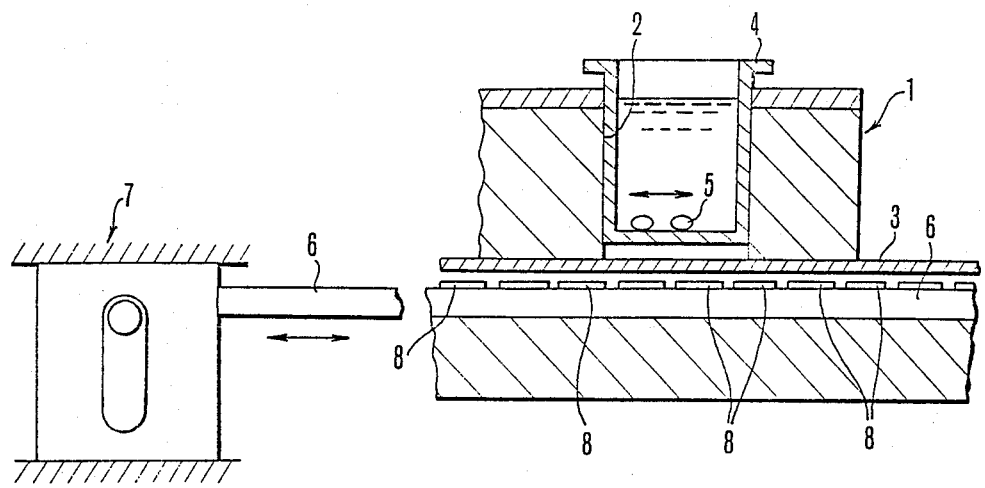
FIGS. 2(a) and 2(b) show constituents of the bead vibrating apparatus.
Figure 2B:
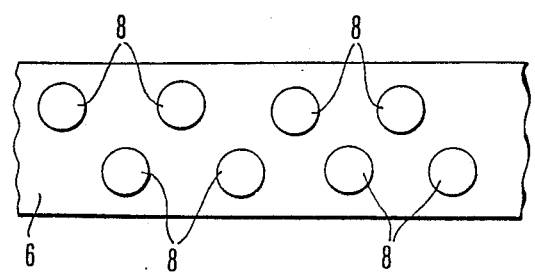

A rod 6 is placed under the conveyance way 3 upon which the test plate 1 is placed, and it is reciprocated along a given stroke in the direction indicated by the arrow in FIG. 2(a) by a cam mechanism 7 which is rotated by a drive motor (not shown in the figure). On this rod 6, a great number of magnets 8 at spacings corresponding to each test cup 4 are fixed as shown in FIG. 2(b), thereby forming magnetic vibrating means.

Due to the reciprocating motion of the rod 6, therefore, beads 5 within the test cup 4 will migrate with circular motion, an elliptic motion or an S-curve motion, depending upon the type of reciprocation of the rod 6.

The optical measuring apparatus, e.g. a well-known microplate fluorescence automatic reader, as schematically shown in FIG. 1, is placed above the test cup 4 and the light A from the light source 20 is measured as a radiating fluorescence B.

That is, the well-known optical measuring apparatus, as shown in FIG. 1, operates as follows:

To the test cup 4 filled with beads 5, on the surface of which the enzyme-linked conjugates are bound due to a specific immune reaction, and an appropriate substrate solution 9 which causes optically detectable changes due to the aforesaid enzyme activity, is applied light from the light source 20 via the excitation side filter 21, a dichroic mirror 22 and the condenser lens 23. The light B from the test cup 4 proceeds in a detecting direction to detecting means including the condenser lens 23, the dichroic mirror 22 and the light receiving side filter 24, and the light is received by the photosensor 25 and a signal processing circuit (not shown) by which the intensity of the detected light will be measured.

According to the known enzyme immunoassay methods, the complex of the first antibody (anti-HCG) on the solid beads—antigen (HCG)—enzyme (alkaline phosphatase) conjugated second antibody (anti-HCG) is formed on the surface of beads, and after the free enzyme conjugated second antibody is removed by B/F separation, a substrate solution (4-methylumbelliferyl-phosphate monoester) which generates fluorescence by the acton of the aforesaid enzyme is added. Subsequently, the above described optical measuring sequence is applied and changes in the intensity of fluorescence occurring in the substrate is measured while vibrating beads 5 by the reciprocating motion of the rod 6, the reciprocating motion having at least a component transverse to the detecting direction.

In such a procedure, since the existence probability of vibrating beads in the limited area for optical measurement within the test cup is evened, averaged or levelled by the vibrations, technical errors which might otherwise arise due to the beads being unevenly arranged in the cell are eliminated.

The present test method, further, has such an effect that vibration of beads produces agitation of the substrate within the cell, hence an apparent increase in the intensityof fluorescence of a substrate due to the enzyme activity occurs in direct proportion to the amount of enzyme, and also has the advantage of more accurate quantitative measurement of enzyme and antigen in the case where the rate of increase in the intensity of fluorescence is measured as a criterion.

EXAMPLE

Ferritin was used as a material to be measured and 12 beads, and 1 mm in diameter, were put in a vessel 8 mm in inner diameter.

Magnets 8, each of which is a round rare-earth magnet, 5 mm in a diameter and 3 mm in thickness are fixed on the rod 6 which is used for vibrating beads and are placed at a pitch of 16 mm and in double lines (the distance between the centers of the magnets in the right and left lines is 5 mm), as shown in FIG. 2(b).

In the first reaction, the antigen-antibody reaction was made for 40 minutes with vibrating (stroke 48 mm, 80 cpm) of the magnet apparatus, and after the B/F separation the enzyme substrate solution was added and changes in the amount of fluorescence (4 methylumbelliferone) decomposed by the enzyme with vibrating (and not vibrating as an experimental control) was measured as the rate of increase in the intensity of fluorescence.

Test results are indicated in Tables 1 and 2. In the determination under vibration, the reproducibility (coefficient of variation CV %) in ten determinations was 7.08% at a 0 concentration of ferritin, 4.45% at a low concentration (L) (about 50 ng/ml), 4.40% at a medium concentration (M) (500 ng/ml), and 3.70% at a high concentration (H) (about 800 ng/ml).

On the contrary, in the determination without vibration (Table 2), the reproducibility was extremely low, 29.53%, 18.26%, 19.11% and 10.14%, respectively.

Under non-vibration conditions, further, the rate of production of fluorescence was small at a high concentration and its linear state was not observed, as it was under vibration. These results are believed to be caused by the diffusion of substrate at the surface of beads being inadequate.

These results indicate that by use of the invention, technical errors in optical determination decrease and high producibility can be obtained under given conditions.

Incidentally, the present embodiment presented a test method measuring the fluorescence intensity of a substrate as an enzyme immunoassay, but this test method may be substituted for by a method measuring the absorbance of the substrate, and also by one using a fluorescent substrate or a luminescent substance instead of an enzyme as a marker. In any of these methods, effects based on the probability of the existence of a bead in a limited area for optical determination within the cell is levelled by vibrating the beads.

The present invention, as mentioned above, will eliminate the problem of technical errors in optical determination derived from the existence of a bead, by vibrating the bead within the cell, and lead to an improvement in accuracy of determination where an extremely small amount of material is quantitatively dealt with. Its advantages will render great service in immunoassay methods.

While a specific embodiment of the present invention has been shown and described in detail to illustrate the application of the inventive principles, it will be understood that the invention may be embodied otherwise without departing from such principles.

TABLE 1

Test Results under Vibration
(The rate of fluorescence intensity)

| Sample Concentration | O | L | M | H |
|---|---|---|---|---|
| 1 | 1.09 | 4.75 | 38.92 | 60.94 |
| 2 | 1.31 | 5.01 | 37.29 | 61.41 |
| 3 | 1.23 | 4.48 | 36.54 | 58.67 |
| 4 | 1.21 | 4.95 | 36.41 | 57.00 |
| 5 | 1.41 | 4.83 | 39.06 | 57.50 |
| 6 | 1.23 | 5.05 | 34.86 | 61.77 |
| 7 | 1.36 | 4.43 | 34.94 | 62.46 |
| 8 | 1.27 | 4.61 | 35.36 | 61.46 |
| 9 | 1.21 | 4.86 | 38.84 | 64.07 |
| 10 | 1.29 | 4.75 | 36.38 | 59.95 |
| AVG No. 1-10 | 1.26 | 4.77 | 36.86 | 60.52 |
| STD | 0.09 | 0.21 | 1.62 | 2.24 |
| CV % | 7.08 | 4.45 | 4.40 | 3.70 |

TABLE 2

Test Results under Non-vibration
(The rate of fluorescence intensity)

| Sample Concentration | O | L | M | H |
|---|---|---|---|---|
| 1 | 0.97 | 4.26 | 28.28 | 44.73 |
| 2 | 0.74 | 4.52 | 25.10 | 35.28 |
| 3 | 1.71 | 5.86 | 20.12 | 48.85 |
| 4 | 0.98 | 5.05 | 34.41 | 44.14 |
| 5 | 1.25 | 4.01 | 27.48 | 44.58 |
| 6 | 1.20 | 3.04 | 19.60 | 41.04 |
| 7 | 0.68 | 4.30 | 30.07 | 45.71 |
| 8 | 1.08 | 5.82 | 27.35 | 36.03 |
| 9 | 1.63 | 4.38 | 25.76 | 42.99 |
| 10 | 1.11 | 4.68 | 35.61 | 46.24 |
| AVG No. 1-10 | 1.14 | 4.59 | 27.38 | 42.96 |
| STD | 0.34 | 0.84 | 5.23 | 4.36 |
| CV % | 29.53 | 18.26 | 19.11 | 10.14 |

What is claimed as new and desired to be secured by Letters Patent of the United States is:

1. In an immuno assay method for optically detecting the complex of an immuno reaction conducted on the surface of a bead, the improvement comprising vibrating said bead so as to average an existence probability of said bead in a cell during the optical detection of the complex.

2. The method of claim 1 including the step of using optical measuring means to quantitatively determine the amount of a marker in said cell, wherein said optical measuring means has detecting means directed towards said cell in a detecting direction, said detecting means being capable of optical measurement in only a limited area of said cell, and wherein said vibrating step comprises vibrating said at least one bead in a direction having at least a component transverse to said detecting direction, whereby the existence probability of said at least one bead in said limited area is averaged over a plurality of said quantitative determining steps.

3. The method of claim 2 wherein said at least one bead is vibrated in a direction transverse to said detecting direction.

4. The method of claim 1 wherein said at least one bead contains a magnetic material and said vibrating step comprises the step of causing a magnetic field to move within said cell.

5. The method of claim 2 wherein said at least one bead contains a magnetic material and said vibrating step comprises the step of causing a magnetic field to move within said cell.

6. The method of claim 5 wherein said vibration has a frequency of from 10 to 800 cycles per minute and an amplitude sufficient to level the existence probability of said at least one bead in said cell.

7. An immunoassay apparatus comprising: means for forming a complex of an immuno reaction conducted on a surface of at least one bead within a cell;
   means for vibrating said at least one bead within said cell; and
   optical means for detecting said immuno reaction.

8. The immunoassay apparatus of claim 7 wherein said optical means comprise detecting means directed towards said cell in a detecting direction, said detecting means being capable of optical measurement in only a limited area of said cell.

9. The apparatus of claim 8 wherein said vibrating means comprise means for vibrating said at least one bead in a direction having a component transverse to said detecting direction and with an amplitude sufficient to level an existence probability of said at least one bead in said cell over a plurality of quantitative determinations by said optical determination means.

10. The apparatus of claim 8 wherein said vibrating means comprises means for vibrating said at least one bead in a direction transverse to said detecting direction and with an amplitude sufficient to level an existence probability of said at least one bead in said cell over a plurality of quantitative determinations by said optical determination means.

11. The apparatus of claim 7 wherein said vibrating means comprise magnetic vibrating means.

12. The apparatus of claim 7 wherein said at least one bead contains a magnetic material and said vibrating means comprises means for causing a magnetic field to move in said cell.

13. The apparatus of claim 9 wherein said at least bead contains a magnetic material and said vibrating means comprises means for causing a magnetic field to move in said cell.

14. The apparatus of claim 12 wherein said means for causing a magnetic field to move in said cell comprises:
   a rod positioned adjacent said cell and having at least one magnet thereon; and
   means for reciprocating said rod.

15. The apparatus of claim 13 wherein said means for causing a magnetic field to move in said cell comprises:
   a rod positioned adjacent said cell and having at least one magnet thereon; and
   means for reciprocating said rod.

* * * * *